United States Patent
Dorsey, III

[11] Patent Number: 5,505,710
[45] Date of Patent: Apr. 9, 1996

[54] TELESCOPING PROBE

[75] Inventor: James H. Dorsey, III, Delray Beach, Fla.

[73] Assignee: C. R. Bard, Inc., Murray Hill, N.J.

[21] Appl. No.: 293,715

[22] Filed: Aug. 22, 1994

[51] Int. Cl.[6] .................. A61M 25/00; A61M 39/00
[52] U.S. Cl. ........................... 604/158; 604/164
[58] Field of Search .................. 604/157, 158, 604/164, 165, 167, 256

[56] References Cited

U.S. PATENT DOCUMENTS

| | | | |
|---|---|---|---|
| 1,527,291 | 2/1925 | Zorraquin | 604/158 |
| 2,623,520 | 12/1952 | Bamford, Jr. et al. | 604/165 |
| 3,515,137 | 6/1970 | Santomieri | 604/165 |
| 3,585,996 | 6/1971 | Reynolds | 604/158 |
| 3,727,613 | 4/1973 | Sorenson et al. | 604/165 |
| 3,792,703 | 2/1974 | Moorehead | 604/158 |
| 4,601,710 | 7/1986 | Moll | 604/165 |
| 4,613,329 | 9/1986 | Bodicky | 604/158 |
| 4,767,407 | 8/1988 | Foran | 604/164 |
| 4,857,057 | 8/1989 | Sanagi | 604/164 |
| 4,911,691 | 3/1990 | Aniuk et al. | 604/158 |
| 4,986,814 | 1/1991 | Burney et al. | 604/164 |
| 5,045,065 | 9/1991 | Raulerson | 604/167 |
| 5,057,085 | 10/1991 | Kopans | 604/158 |
| 5,163,912 | 11/1992 | Gay et al. | 604/164 |
| 5,226,426 | 7/1993 | Yoon | 604/165 |

*Primary Examiner*—Paul J. Hirsch
*Attorney, Agent, or Firm*—Malin, Haley, DiMaggio & Crosby

[57] ABSTRACT

A telescoping surgical probe is disclosed which allows the user to accomplish various functions including several suction techniques and irrigation with a single surgical probe. The telescoping probe includes an inner cannula operatively associated with an outer cannula. The telescoping probe is used with a valve including trumpet valves.

24 Claims, 8 Drawing Sheets

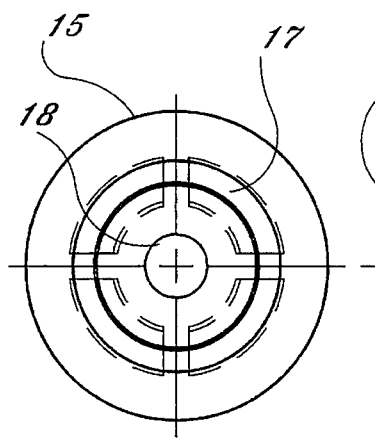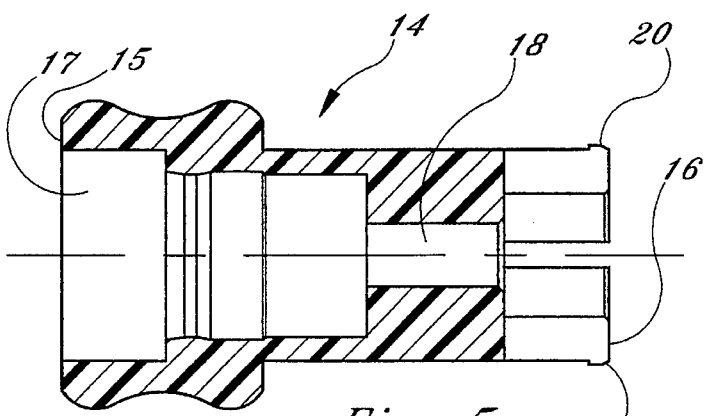
Fig. 5b     Fig. 5a
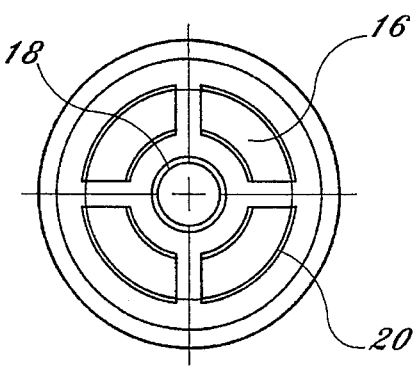
Fig. 5c
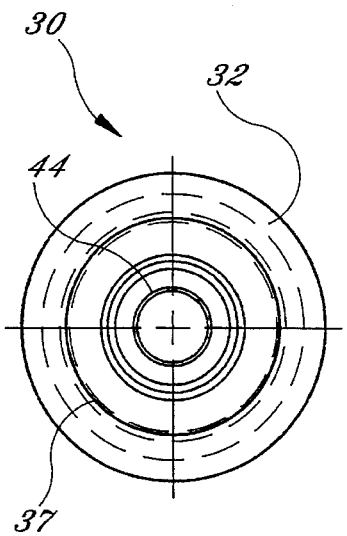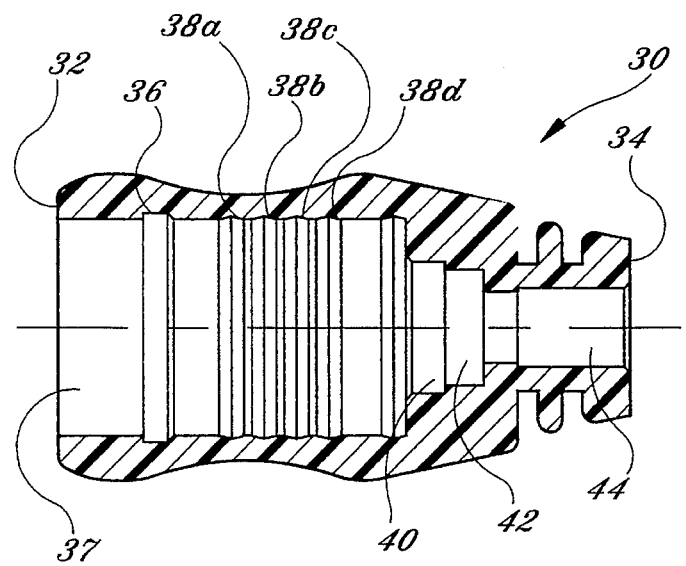
Fig. 6b     Fig. 6a

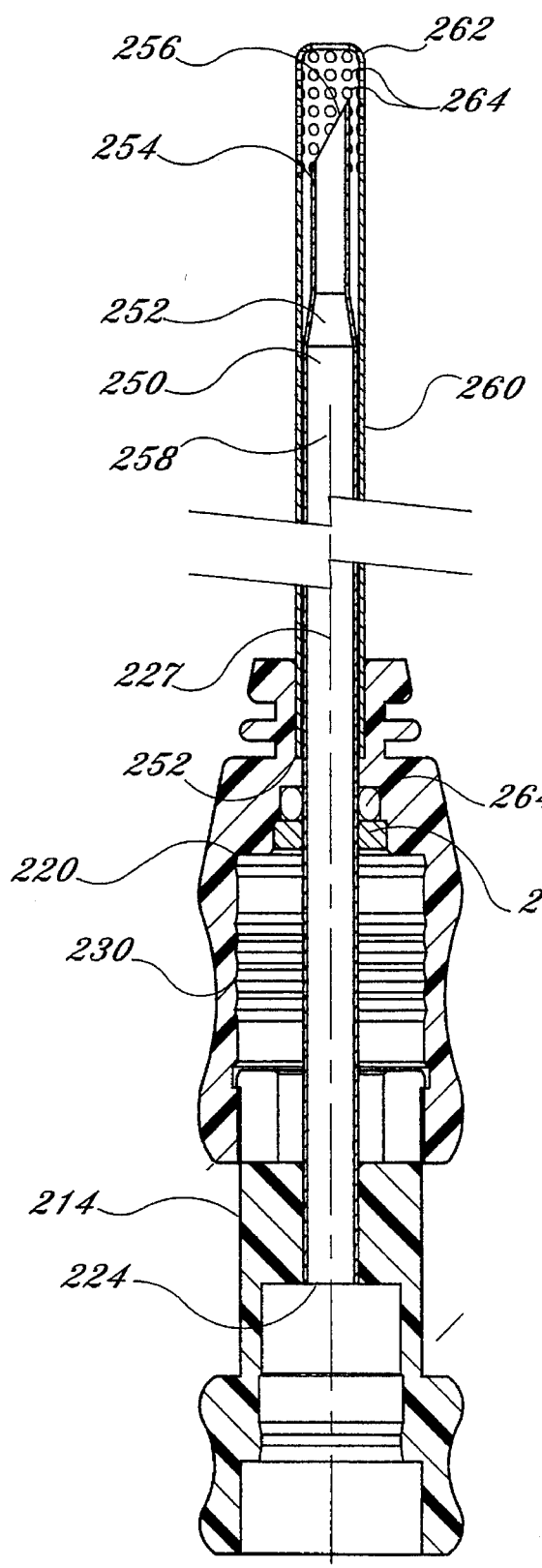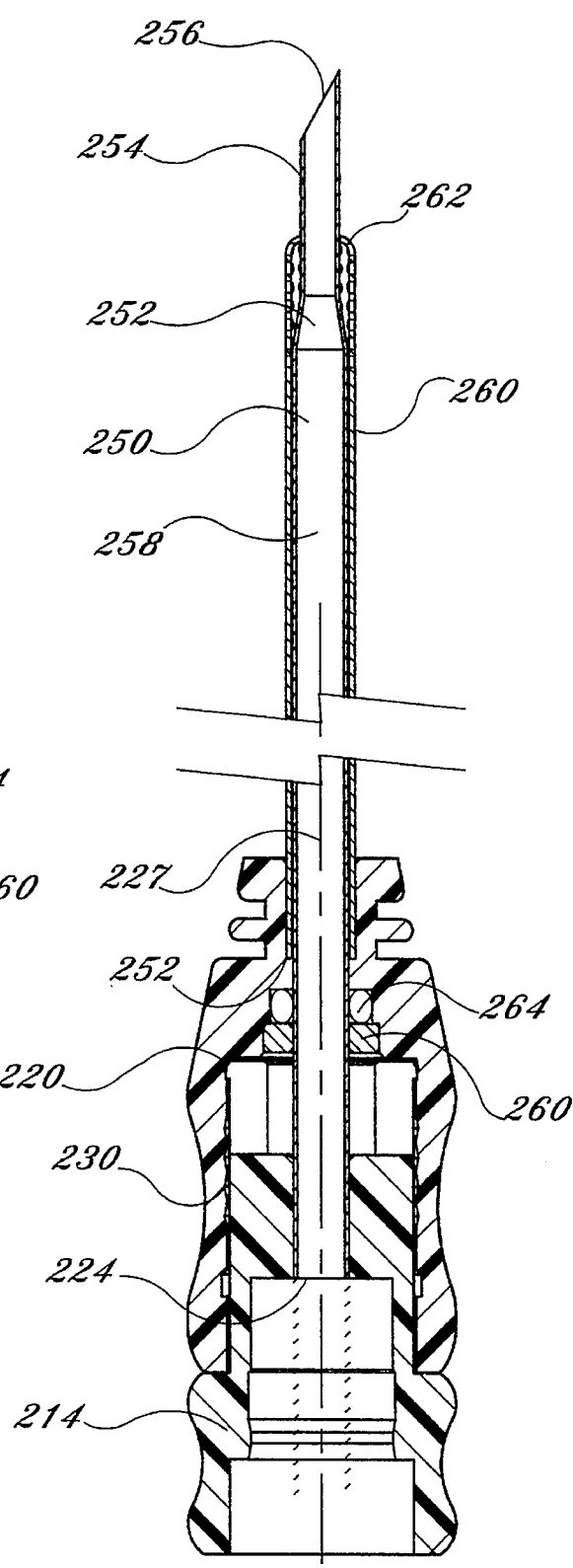

TELESCOPING PROBE

BACKGROUND OF THE INVENTION

1. Field of the Invention

The present invention relates generally to endoscopic/laparoscopic instruments, and more particularly, to a telescoping surgical probe.

2. Description of the Prior Art

Hydrodissection procedures typically involve directing a pressurized fluid stream at a target tissue through a probe, followed thereafter by suction of the fluid from the operative field through the same probe; or, through a probe connected to a separate instrument. This procedure, as practiced with a symmetrical valve of the type disclosed in U.S. Pat. No. 5,188,591, simply involves the sequential depression of the irrigation piston connected to the source of the hydrodissection fluid, release of the irrigation piston, which discontinues the flow of fluid, depression of the suction piston to effect aspiration of fluid from the operative field, and the repetition of the above sequence.

In the past various probes have been utilized for various suction and irrigation situations that arise during the operative procedure. Such situations include the clearing of different depth levels of blood located at the operative field, suctioning of tissue and other debris, or the use of suction and irrigation to move or dissect various organs or adhesions at or near the operative field. Thus, each time a different need arisen for suction or irrigation which could not be accomplished by the probe attached to the valve, such probe had to be removed from the valve and replaced with the appropriate probe. Accordingly, valuable surgical time is wasted by the replacement of one probe for another.

What is needed in the art is a single surgical probe which contains the various suction tips and their companion uses and features described above, as well as irrigation oriented probe tips, thus, allowing the user to perform various tasks with suction or irrigation with the use of a single probe. It is, therefore, to the effective resolution of the aforementioned problems and shortcomings that the present invention is directed.

SUMMARY OF THE INVENTION

The present invention provides a telescoping surgical probe which allows an inner cannula to be positioned in relationship to an outer cannula from a closed position to an open position and any position therebetween. The inner cannula contains a hollow probe shaft connected to a probe shaft housing. The outer cannula also contains a hollow probe shaft and a probe shaft housing. The diameter of the outer probe shaft is larger than the diameter of the inner probe to allow the inner probe shaft to be inserted within the outer probe shaft. In one configuration, a plurality of apertures are disposed near one end of the inner probe shaft.

In the invention first embodiment, how far the inner probe shaft has been inserted within the outer probe shaft, will determine how many of the plurality of apertures extend out the non-inserted end of outer probe shaft, if any at all. In one embodiment, a spring actuated button having a retainer member attached thereto is disposed at the base of the outer probe shaft. A portion of the retainer member extends within a slot disposed on a portion of the base of the inner probe to guide and lock the inner probe shaft with respect to the outer probe shaft.

In another embodiment, a plurality of grooves can be provided on the inner surface of the outer probe shaft housing which, in conjunction with a detent or chamfer disposed on the inner shaft housing, aid the user in exposing only the amount of apertures required for the desired function of the probe. The detent, in conjunction with another groove disposed on the inner surface of the probe shaft housing, also helps prevent the inner probe shaft from becoming accidentally removed or dislodged from the outer probe shaft.

Accordingly, the present invention provides a single probe which can convert to a probe tip with holes or to a probe tip without holes.

It is therefore an object of the present invention to provide a surgical probe which can perform various suction functions.

It is another object of the present invention to save surgical time during hydrodissection procedures.

It is still another object of the present invention to eliminate the need to switch surgical probes for various suction situations.

In accordance with these and other objects which will become apparent hereinafter, the instant invention will now be described with particular reference to the accompanying drawings.

BRIEF DESCRIPTION OF THE DRAWINGS

The invention may be better understood by reference to the drawings in which:

FIG. 5a is a sectional view of the inner probe shaft housing of the present invention;

FIG. 5b is a back view of the inner probe shaft housing of the present invention;

FIG. 5c is a front view of the inner probe shaft housing of the present invention;

FIG. 6a is a sectional view of the outer probe shaft housing of the present invention;

FIG. 6b is a back view of the outer probe shaft housing of the present invention;

FIG. 9 is a sectional view of the present invention in a fully retracted position for a second alternative surgical probe embodiment;

FIG. 10 is a sectional view of the present invention in a fully extended position for a second alternative surgical probe embodiment;

DESCRIPTION OF THE PREFERRED EMBODIMENTS

Figure 1:
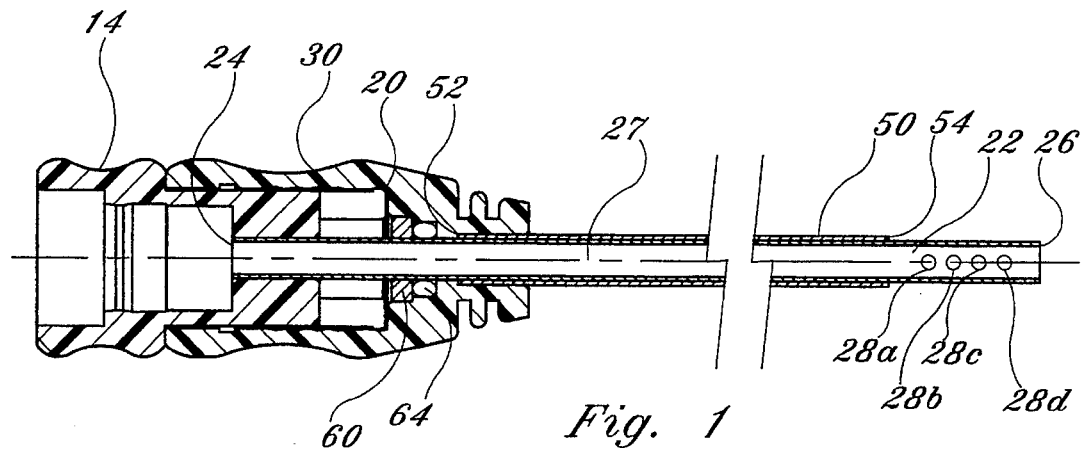
FIG. 1 is a sectional view of the present invention in a fully extended position.

FIGS. 1 through 6 illustrates a first embodiment of the present invention. The telescopic probe is generally shown at 10 and includes an inner cannula or barrel 12 operatively associated with an outer cannula or barrel 13. Probe 10 is removeably attached to a (trumpet) valve (not shown) by various conventional methods, including the quick disconnected method which is the subject matter of my application Ser. No. 07/989,109, filed on Dec. 11, 1992. The subject matter Ser. No. 07/989,109 is hereby incorporated by reference in its entirety into the instant application as if fully set forth herein.

Inner cannula 12 includes an elongated hollow probe shaft or tube 22 having a first end 24 and a second end 26 and defining an internal passageway 27 extending from first end 24 to second end 26. In one shaft design, groups of holes 28a, 28b, 28c and 28d are disposed along shaft 22 near second end 26. First end 24 is housed by a first probe shaft housing or base 14. As seen in FIG. 5a, housing 14 includes a first end 15, a second end 16 and a first shaft receiving cavity 18 for receiving first end 24 of shaft 22. Shaft 22 is connected to housing 14 by inserting first end 24 into cavity 18 which tightly receives and retains first end 24 therein. Cavity 18 communicates with a valve connecting channel 17. Thus, when inner cannula 12 and outer cannula 13 are in proper relationship with each other, discussed in detail below, probe 10 is connected to a valve (not shown) by inserting a probe connection portion of the valve within channel 17. One connection method is the quick disconnect method discussed above. Once connected, during suction blood, debris and other material properly travel through internal passageway 27 of shaft 22 and through channel 17 of housing 14 to the connected valve. Furthermore, during irrigation fluid travels through internal passageway 27 from the connected valve.

Outer cannula 13 includes an elongated hollow probe shaft or tube 50 having a first end 52 and a second end 54 and defining an internal passageway 55 extending from first end 52 to second end 54. The diameter and length of shaft 50 is sized to receive a substantial portion of hollow probe shaft 22 of inner cannula 12, discussed in detail below. First end 52 is housed by a second probe shaft housing or base 30. As seen in FIG. 6a, housing 30 contains a second shaft receiving cavity 44 for receiving first end 52 of shaft 50. Shaft 50 is connected to housing 30 by inserting first end 52 into cavity 44 which tightly receives and retains first end 52 therein. Cavity 44 communicates with an inner cannula receiving channel 37. Disposed between cavity 44 and channel 37 can be additional channels 40 and 42. Channel 40 receives a retainer ring 60, while channel 42 receives a sealing means. Preferably, sealing means is an o-ring 64.

Retaining ring 60 and o-ring 64 each have associated centerholes 62 and 66 respectively extending therethrough. Centerholes 62 and 66, allow rings 60 and 64, respectively, to be disposed along the outer surface of inner probe shaft 22 when in use.

Figure 2:
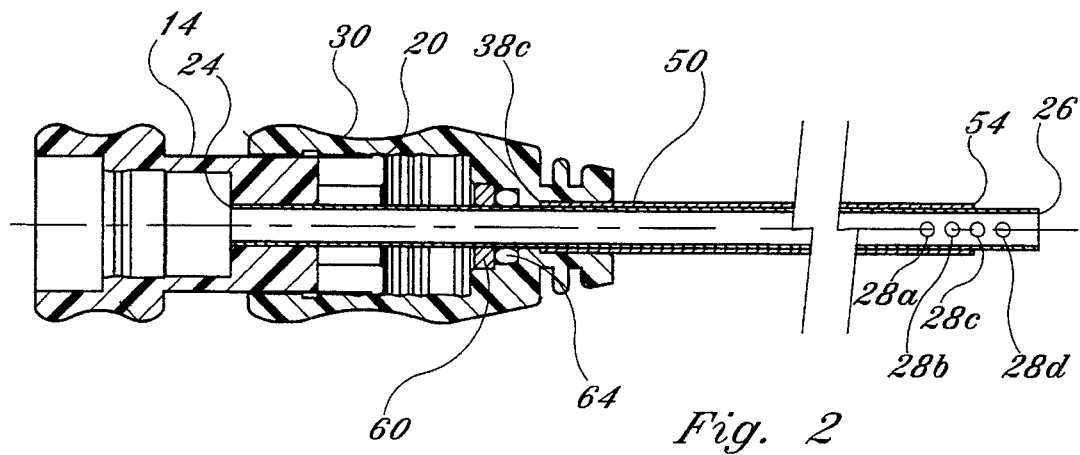
FIG. 2 is a sectional view of the present invention in an intermediate position.
Figure 3:
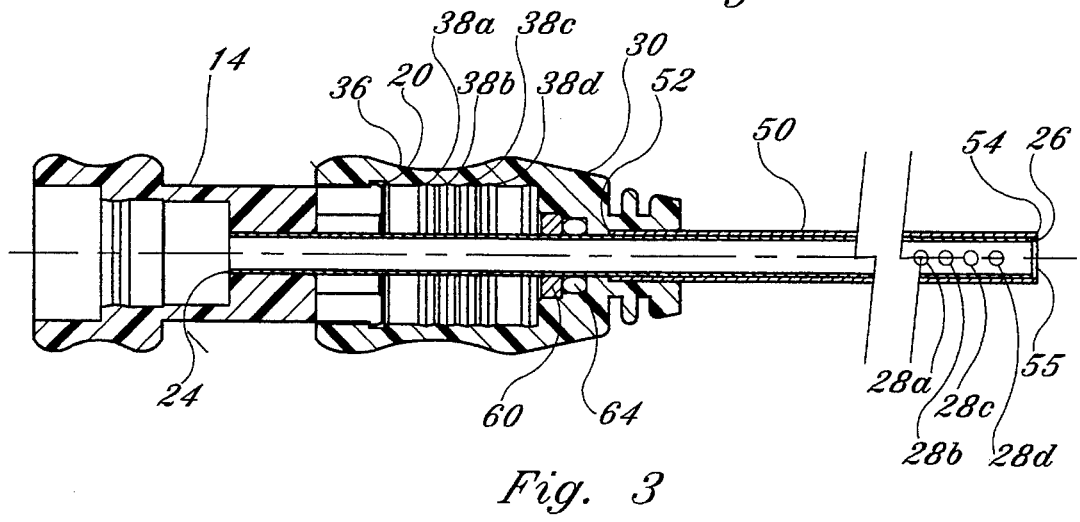
FIG. 3 is a sectional view of the present invention in a fully retracted position.
Figure 4:
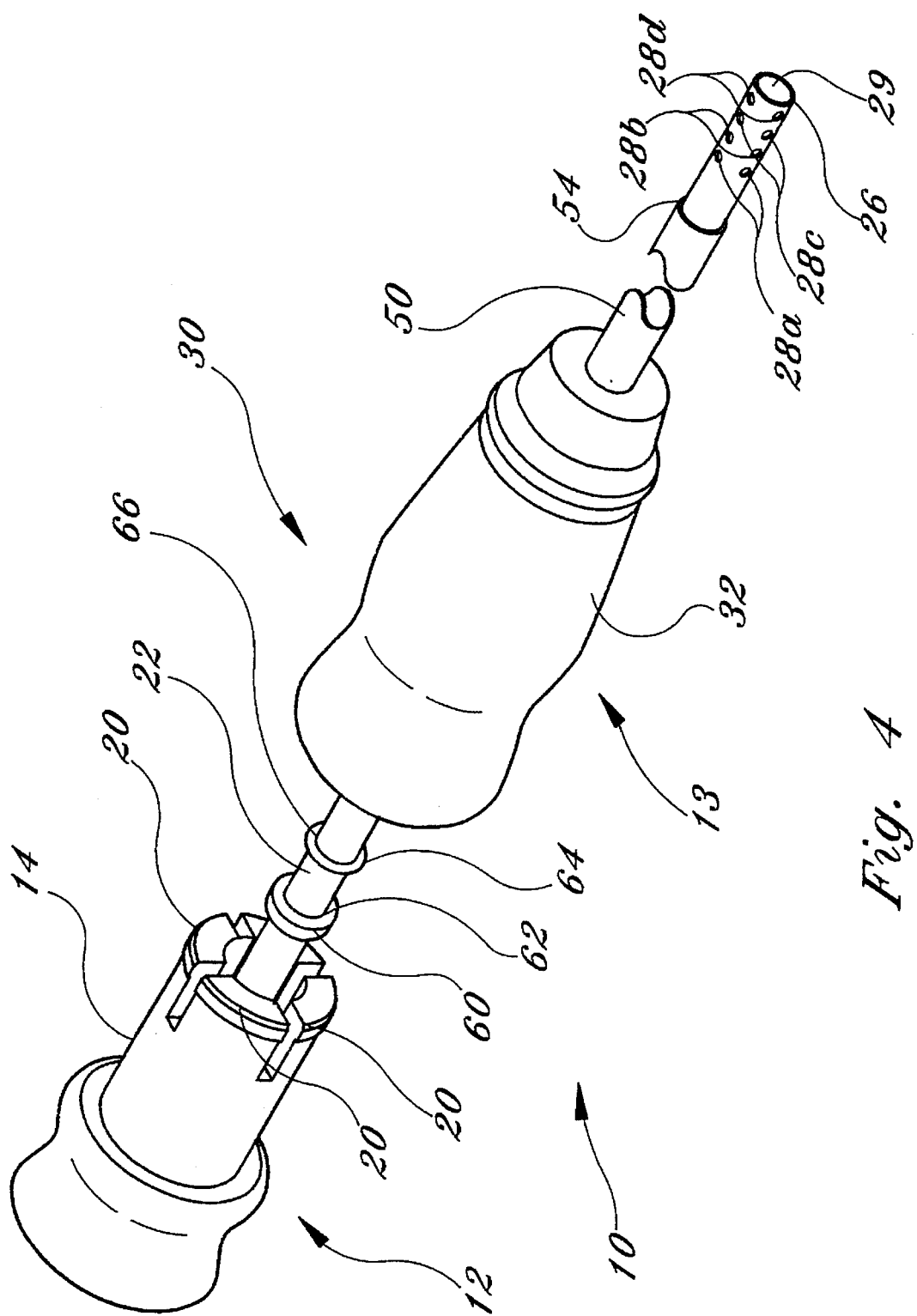
FIG. 4 is an isometric view of the present invention.

As seen in FIGS. 1 through 3, the present invention allows inner cannula 12 to be disposed at various positions in relation to outer cannula 13. In operation, inner probe shaft 22 is connected to housing 14 and outer probe shaft 50 is connected to housing 30 as previously discussed. End 26 of inner probe shaft 22 is inserted through channels 37, 40 and 42, and internal passageway 55 of outer probe shaft 50. Once inserted, end 26 of inner probe shaft 22 can be protruding out of second end 54 of outer probe shaft 50 at various lengths, depending on the function desired from the composite probe 10. Thus, in FIG. 1 inner probe shaft 22 is fully extended out and all of the groups of holes 28a–28d along end 26 of inner shaft 22, as well as aperture 29 at end 26, are utilized in suctioning blood, debris, contaminants and other materials. This inner probe shaft position is particularly used for clearing out pools of blood to enhance the user visibility of the surgical area of the body.

FIG. 2 shows inner probe shaft 22 in an intermediate position between fully extended (FIG. 1) and fully retracted (FIG. 3). In this intermediate position only some of the group of holes 28c and 28d are available for suctioning. This inner probe shaft position is also primarily used for clearing pools of blood disposed at the operative field. However, such pools of blood would have depth levels less than those discussed in the preceding paragraph. Accordingly, only some and not all of the group of holes 28 are needed for sufficient suctioning.

In one embodiment of the telescoping means of the present invention, a plurality of internal grooves 38a, 38b, 38c and 38d are disposed on a portion of the inner surface of channel 37. Grooves 38a–38d are used as indicating means and are associated with group of holes 28a–28d, respectively, of inner probe shaft 22 to indicate to the user how many of group of holes 28 are exposed for suctioning purposes. Though four group of holes 28a–28d and four internal grooves 38a–38d are shown, the present invention is not limited to such and any number of holes and corresponding grooves are within the scope of the present invention.

Thus, in operation and in the fully retracted position (FIG. 3), the movement of inner cannula 12 forward causes detent 20 to travel over groove 38a and provides a click. At this point, only hole 28a will be exposed from out of outer probe shaft 50 for suctioning. Further forward movement of inner cannula 12 causes detent 20 to travel over groove 38b. At this point groups of holes 28a and 28b are exposed from out of outer probe shaft 50. Thus, the number of grooves 38 that detent 20 travels over during the forward movement of inner cannula 12 will indicate to the user how many groups of holes are exposed for suctioning. Once detent 20 has traveled over all of internal grooves 38, all of the groups of holes 28 are exposed and able to be used for suctioning.

Furthermore, if the direction of movement of inner cannula 12 is reversed, each time detent travels over a groove 38, one less number of group of holes 28, than was previously exposed, are available for suctioning. Further reverse traveling by inner cannula causes, accordingly, reduces the number of groups of holes which are exposed until all such groups are disposed within outer probe shaft 50 and unavailable for suctioning (FIG. 3).

As mentioned in the previous paragraph, FIG. 3 shows inner probe shaft 22 in its fully retracted position. In this position, end 26 of inner probe shaft 22 is completely disposed within the internal passageway 55 defined by outer probe shaft 50. This position is desirable for maximum suction and maximum irrigation. Further, this position can also be used to move around or grab onto various organs at or near the operative field. Composite probe 10 can be provided with a stoppage means to prevent inner canula 12 from being accidentally or inadvertently removed or dislodged from outer cannula 13. Preferably, the stoppage means includes the detent or ridge 20, previously discussed, provided at the inner shaft receiving end 16 of inner shaft housing 14. Detent 20 mates with a corresponding groove 36 disposed within the inner surface of outer shaft housing 30, intermediate internal grooves 38 and first end 32 of outer housing 30.

As seen in FIG. 3, when inner shaft 22 is fully retracted within outer probe shaft, detent 20 is disposed within and mating with groove 36 to retain inner shaft 22 within outer shaft 50 and prevent accidental or inadvertent removal or dislodging of such. However, when it is desired to remove inner shaft 22 from outer shaft 50, sufficient pressure or force exerted by the user will allow detent 20 to pass over groove 36, thus, allowing the removal of inner probe shaft 22.

As seen in FIGS. 1–3 retaining ring 60 is shown disposed along inner probe shaft 22 and received within channel 40. Preferably, retaining ring 60 is constructed from metal, aluminum, steel, etc. Retaining ring 60, along with o-ring 64, provides tension when inner cannula 12 is move in relation to outer cannula 13 as described above. Furthermore, o-ring 64 acts as a seal and prevents any blood or debris which may travel through outer probe shaft 50 between the inner surface of shaft 50 and the outer surface of shaft 22 from ultimately entering the associated (trumpet) valve.

When it is desirable to change the position of the cannula 12 with respect to cannula 13 and probe 10 is connected to a valve, outer cannula 13 is moved in relation to fixed inner cannula 12 by either rotating, pushing or pulling outer cannula. However, if probe 10 is not connected to the valve either cannula 12 or 13 can be moved by rotating, pushing or pulling with respect to the other cannula 13 or 12.

Thus the present invention allows the user to perform various suctioning functions with a single probe and, thus, without the need to change probes for each various suction function. The present invention can be incorporated into other probe designs besides the probe illustrated herein, including probes having electrodes and catheters. Thus, these other probe designs incorporating the teachings of the present invention are also within the scope of the invention.

Figure 7:
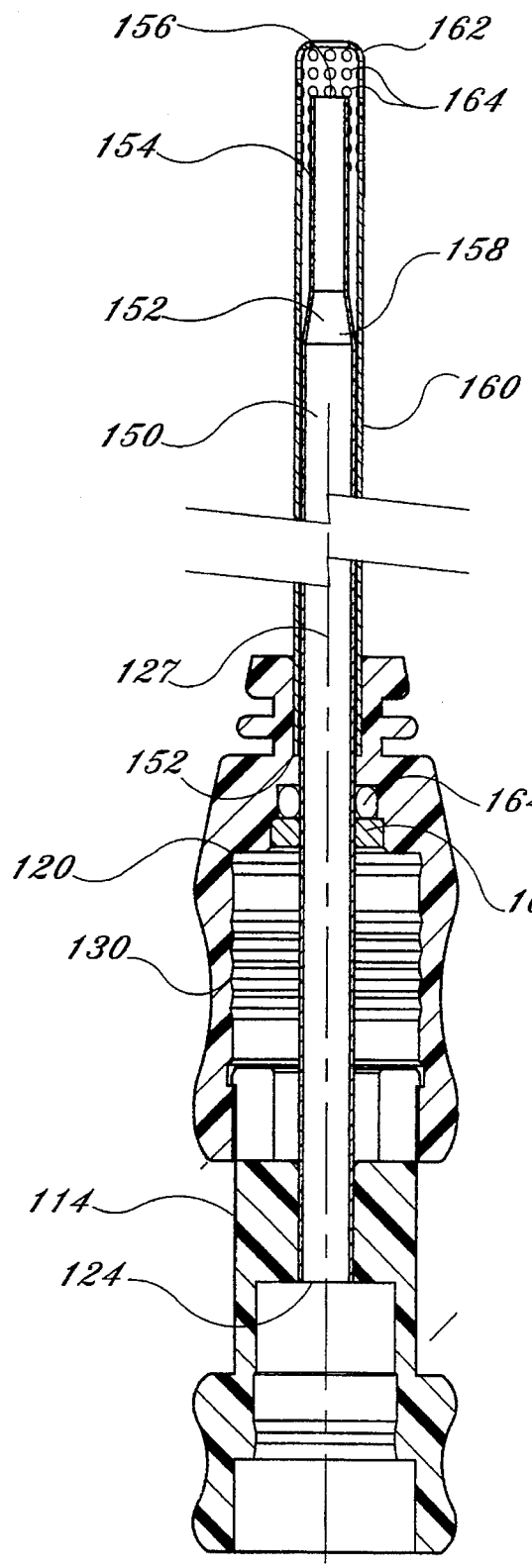
FIG. 7 is a sectional view of the present invention in a fully retracted position for an alternative surgical probe embodiment.
Figure 8:
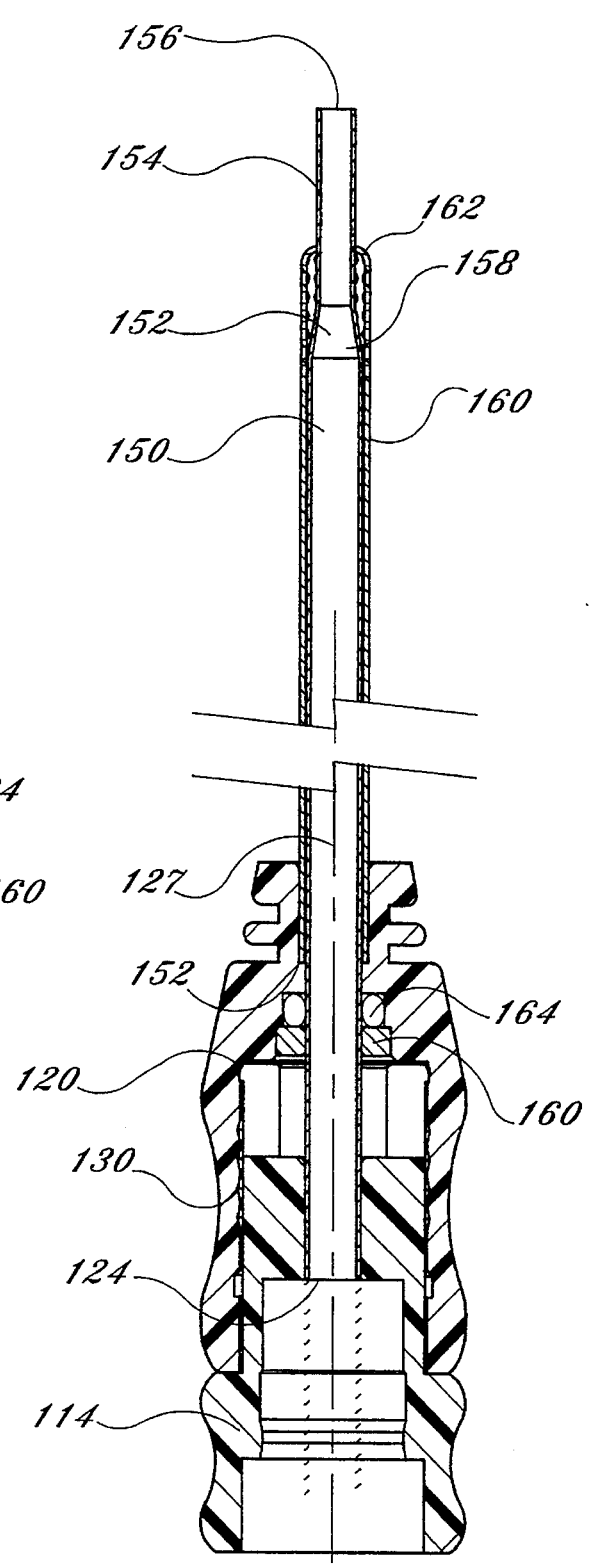
FIG. 8 is a sectional view of the present invention in a fully extended position for an alternative surgical probe embodiment.
Figure 11:
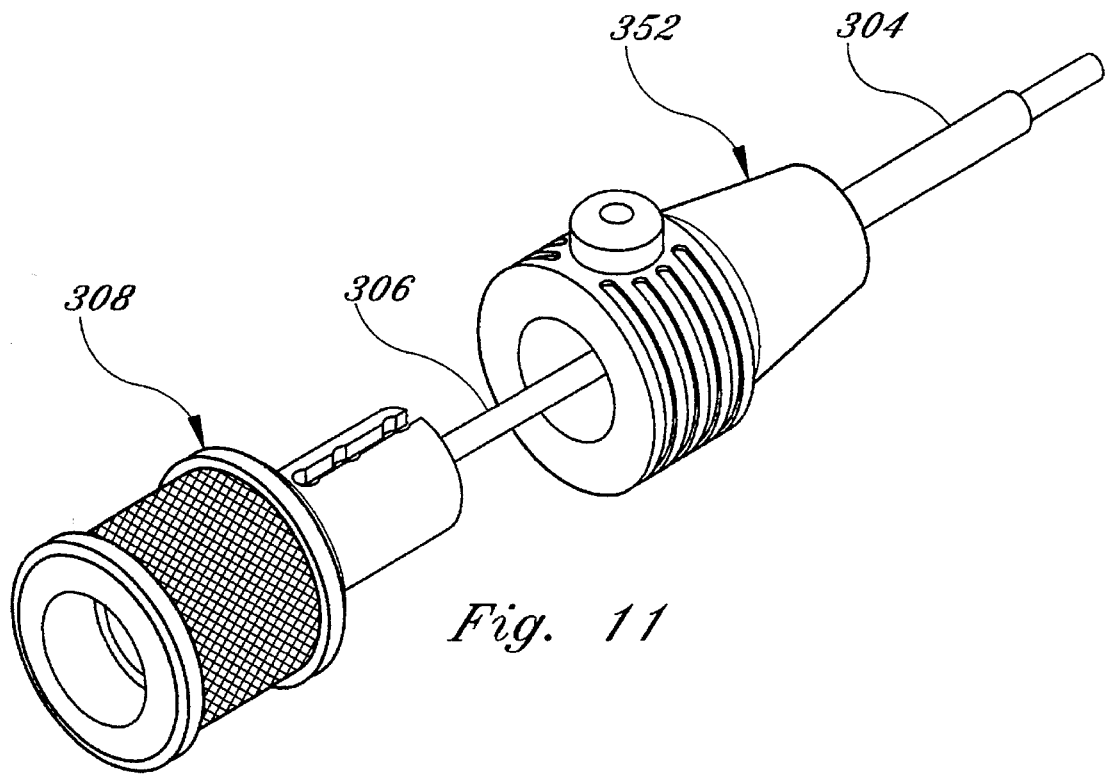
FIG. 11 is a perspective view of the preferred embodiment for the telescoping portion of the present invention.
Figure 12:
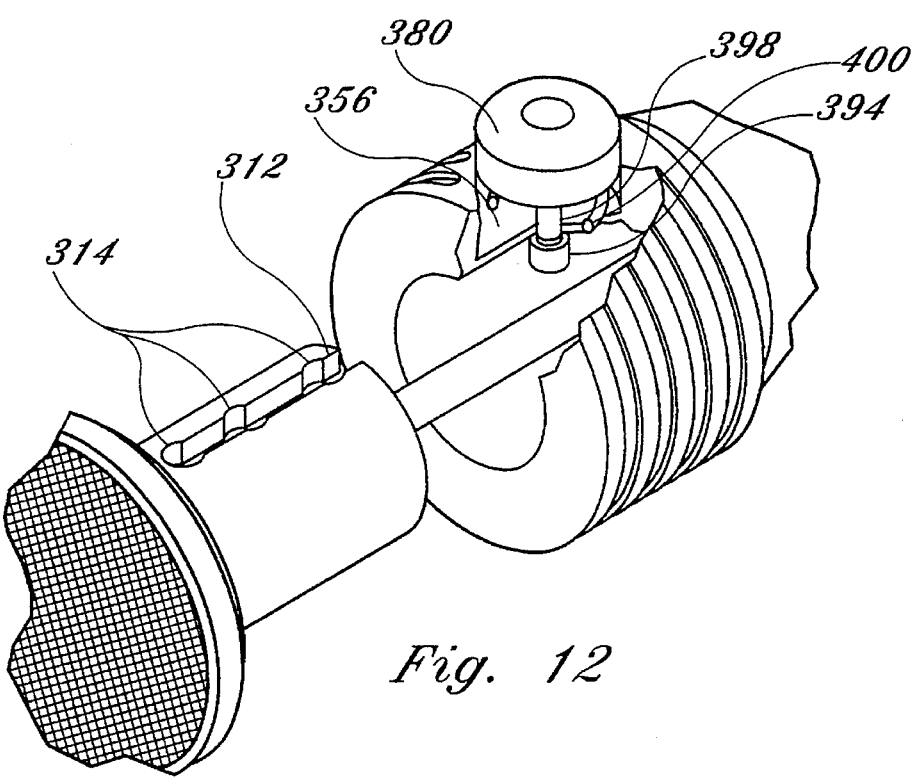
FIG. 12 is a close up perspective view of the invention shown in FIG. 11.

For example, FIGS. 7 through 10 illustrate two different surgical probe embodiments which incorporate the telescoping features of the present invention. FIGS. 7 and 8 illustrate an alternative surgical probe embodiments from that shown in FIGS. 1 through 6. In this embodiment the inner cannula 127 consists of elongated portion 150, tapered portion 152 and flat end portion 154, collectively defining an internal passageway 158. The first end of inner cannula 127 is encompassed by inner housing 114 similar to the probe shown in FIGS. 1 through 6. A majority portion of inner cannula 127 is flushly disposed or fitted within outer cannula 160. Outer cannula 160 defines an internal passageway and has a plurality of holes 164 and an opening 162 at its operative end.

In its fully retracted position (FIG. 7), flat end portion 154 is seen fully disposed within outer cannula 260, while in its fully extended portion, a substantial portion of flat end portion 154 is seen extending outward through opening 162. This embodiment of the present invention, operates similar to the embodiment shown in FIGS. 1 through 6, to allow inner cannula 127 to be disposed in relation to outer cannula 160 anywhere from a fully retracted to a fully extended position and any point therebetween. Furthermore, the locking features and indicators 130 also function similar to the embodiment shown in FIGS. 1 through 6.

FIGS. 9 and 10 illustrate a second alternative surgical probe embodiments from that shown in FIGS. 1 through 6. In this embodiment the inner cannula 227 consists of elongated portion 250, tapered portion 252 and tapered end portion 254, collectively defining an internal passageway 258. The first end of inner cannula 227 is encompassed by inner housing 214 similar to the probe shown in FIGS. 1 through 6. A majority portion of inner cannula 227 is flushly disposed or fitted within outer cannula 260. Outer cannula 260 defines an internal passageway and has a plurality of holes 264 and an opening 262 at its operative end.

In its fully retracted position (FIG. 9), tapered end portion 254 is seen fully disposed within outer cannula 260, while in its fully extended portion, a substantial portion of tapered end portion 254 is seen extending outward through opening 262. This embodiment of the present invention, operates similar to the embodiment shown in FIGS. 1 through 6, to allow inner cannula 227 to be disposed in relation to outer cannula 260 anywhere from a fully retracted to a fully extended position and any point therebetween. Furthermore, the locking features and indicators 230 also function similar to the embodiment shown in FIGS. 1 through 6.

The surgical probe embodiment shown in FIGS. 9 and 10 is used to penetrate into an acute gall bladder or cyst to aspirate out the bile or contents prior to surgery. This is helpful due to the fact that many times acute gall bladders or cysts will rupture during surgery and spill bile and gall stones or cystic fluid throughout the abdominal cavity. These liquids are difficult to clean up later and are also acidic or dirty, thus, having a negative effect on the patient postoperatively. Gynecological laparoscopic cysts, such as chocolate cysts, dermoid cysts and ovarian cysts can also be aspirated in the same manner. The sharpened inner cannula will penetrate into the inner lumen of the cyst or organ and then is retracted back as shown in FIG. 9. The outer cannula acts as a strainer to allow the suction of liquid, but not particulate matter. Irrigation can be squirted inside the lumen to dilute and lower the viscosity of the fluid which makes it easier to suction and cleanse the inner contents of the cyst or organ.

In these alternative surgical probe embodiments (FIGS. 7 through 10), the inner and outer cannulas of the probe are flush fitted except for the end of the assembly where the inner cannula swages into a smaller diameter. Because of such flush fitting, the probe will aspirate and irrigate through the inner cannula only. These probes are used in situations where the physician is aspirating a cyst or some other liquid filled tissue. This is done with the sharpened tapered probe (inner cannula 227 extended out of opening 262), beyond the perforated sheath and aspirating with it as if it were an aspiration or injection needle. By advancing the outer probe and covering the needle, the user can use the same probe assembly as a pool sucker to aspirate and other liquid that may have puddled in the area adjacent to the aspiration site.

FIGS. 11 through 18 illustrate the preferred embodiment for the telescoping means 300 of the present invention. Like FIGS. 1 through 3, telescoping means allows an inner cannula 302 to be disposed at various positions in relation to an outer cannula 304. In operation, an inner probe shaft 306 is connected to an inner base housing 308 and an outer probe shaft 350 is connected to an outer base housing 352. Outer base 352 defines a receiving channel 360 for receiving a portion 310 of inner base 308. End 310 of inner probe shaft 306 is inserted through an internal passageway of outer probe shaft 304. Once inserted, end 310 of inner probe shaft 306 can be protruding out of a second end 354 of outer probe shaft 350 at various lengths, depending on the function desired, similar to composite probe 10 of FIGS. 1 through 3.

A button receiving cavity 356 communicates with a channel 358 to create a passageway through outer base 352. A portion of a button 380 is disposed within cavity 356. Button 380 defines a retainer attachment cavity 382 which is in communication with a spring receiving cavity 384, also defined by button 380. A first end 392 of a retaining pin 390 is inserted within cavity 382 and attached to button 380 by conventional means such as gluing. Pin 390 has an outer lip 394 disposed at its second end 396. Lip 394 is larger in diameter than the remaining area of pin 390 and is also larger in diameter than the diameter of channel 358. Ends 392 and 396 define therebetween a middle pin area 398 having a predetermined length.

Before attaching end 392 to button 380, a portion of a spring 400 is disposed within cavity 356 and the remaining portion of spring 400 extends outward from outer base 352. Pin end 392 is inserted through channel 358 and cavity 356, as well as spring 400, and ready for attachment to button 380. A portion of button 380 is disposed within cavity 356, such that the portion of spring 400 extending out from outer base 352, is received within button cavity 384 and pin end 392, which is received within cavity 382 and subsequently attached to button 380, preferably by gluing. In use, spring 400 is bordered at one end by the bottom surface of cavity 356 and at its opposite end by the bottom surface of button cavity 384 and is disposed around a portion of middle area 398 of retaining pin 390.

Figure 13:
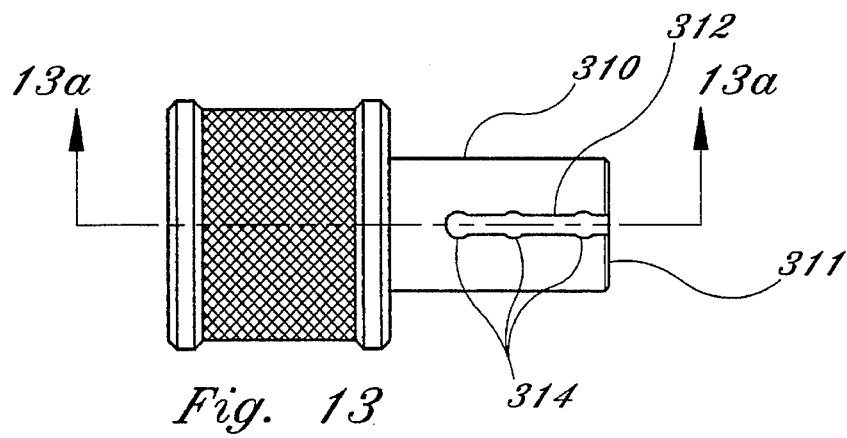
FIG. 13 is a top plan view of the inner base member of the invention shown in FIG. 11.
Figure 13A:
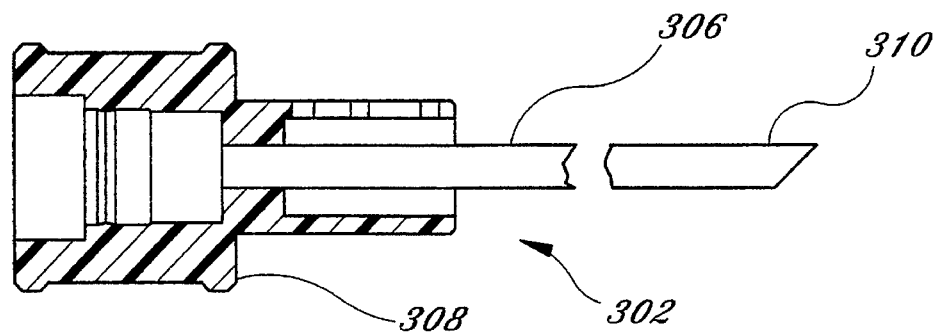
FIG. 13A is a sectional view taken along section line A—A of FIG. 13.
Figure 14:
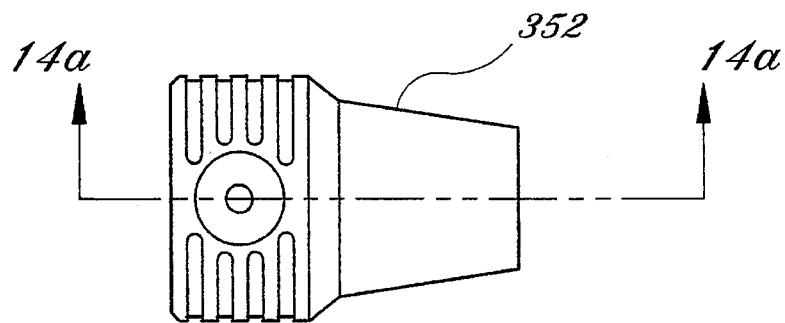
FIG. 14 is a top plan view of the outer base member of the invention shown in FIG. 11.
Figure 14A:
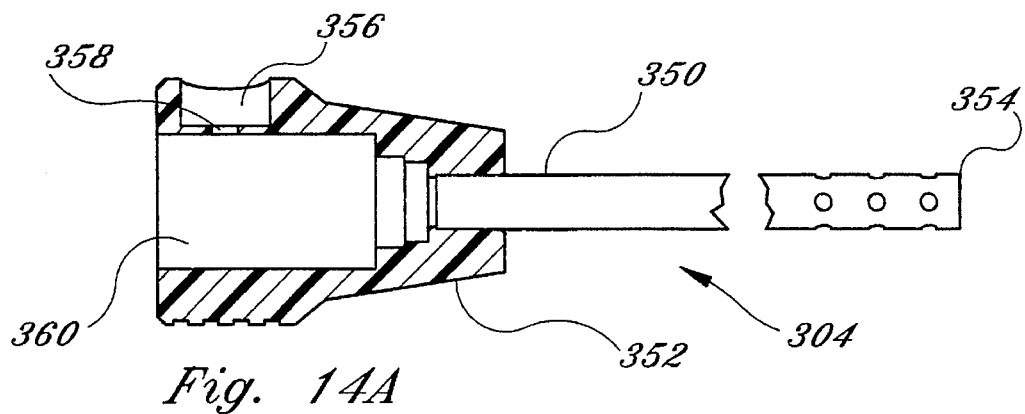
FIG. 14A is a sectional view taken along section line B—B of FIG. 14.
Figure 15:
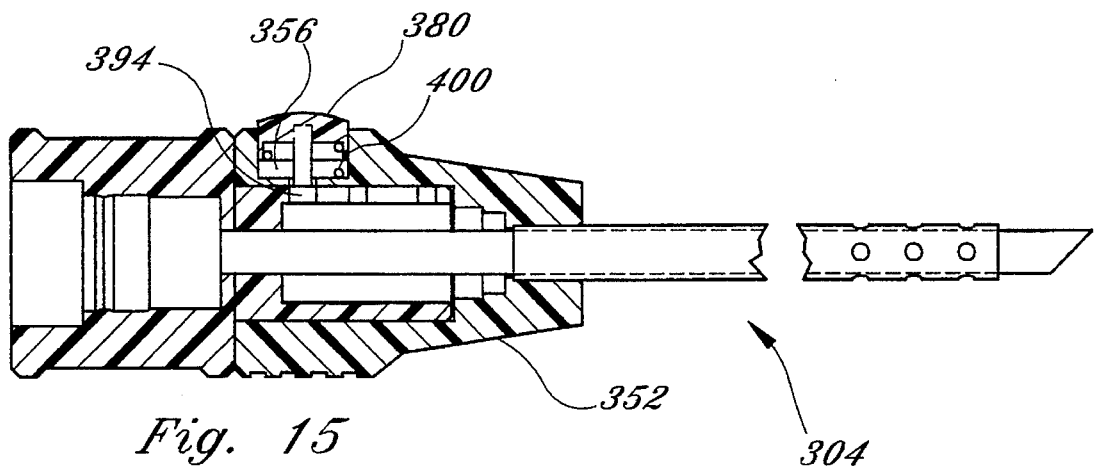
FIG. 15 is a sectional view of the invention shown in FIG. 11.
Figure 16:
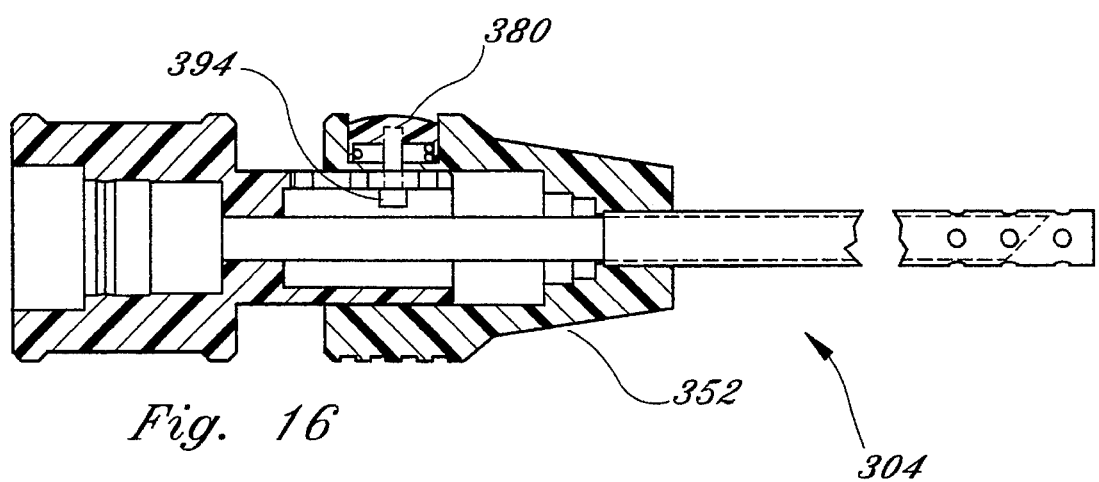
FIG. 16 is a sectional view of the invention shown in FIG. 11 in an intermediate position.
Figure 17:
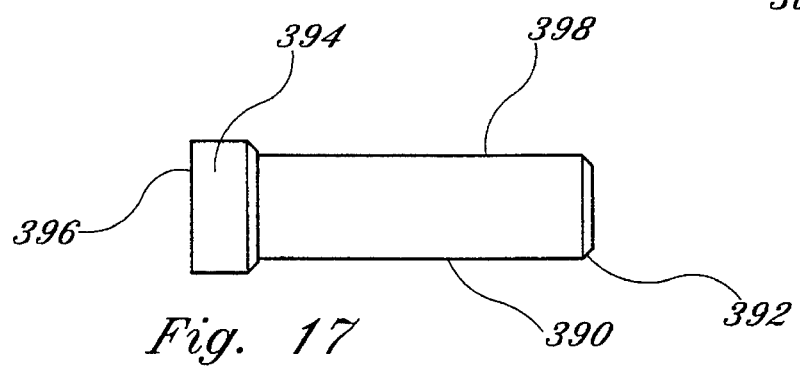
FIG. 17 is a side elevational view of the retainer member of the invention shown in FIG. 12.
Figure 18:
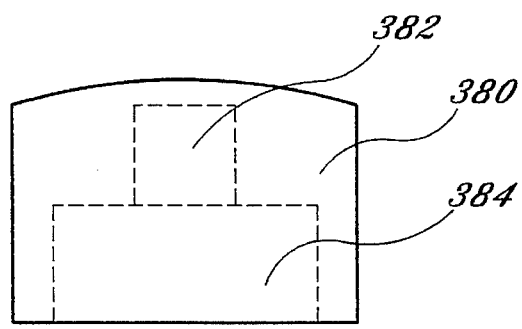
FIG. 18 is a side elevational view of the button member of the invention shown in FIG. 12.

As seen in FIGS. 13 and 13A, portion 310 of inner base 308 has a slot 312 extending along a substantial portion of the length of portion 310. Cylindrical openings 314 are disposed at predetermined locations along slot 312, for receiving lip 394 and a small portion of middle area 398, adjacent lip 394, during use of telescoping means 300. Openings 314 are chosen cylindrical to correspond with the cylindrical shape of lip 394. However, it is to be understood that other shapes can be utilized for openings 314 and lip 394 and are within the scope of the present invention. The distance spanning across slot 312 is slightly smaller between the length of slot 312 bounded by the last opening 314 and end 311 of portion 310 and the remaining length of slot 312. This feature helps to prevent inadvertent or accidental detachment of the outer probe from the inner probe during use of the composite probe.

In use, inner probe shaft 306 is inserted through outer base 352 and within outer probe shaft 350 until end 311 of portion 310 is abutting lip 394 and slot 312 is aligned with lip 394. At this point, button 380 is in an upright position as spring 400 is fully extended. The diameter of lip 394 is larger than distance across slot 312, thus preventing lip 394 from entering slot 312, even when force is applied. However, the pressing of button 380 also causing spring 400 to compress, allows a portion of middle area 398 to be aligned with slot 312. This area is smaller in diameter than lip 394 and upon a little force by the user, allows retainer 390 to enter slot 312.

If retainer 390 is disposed within any of openings 314, one button 380 is no longer pressed, button 380 will pop up and return to its upright position. Spring 400 is designed to fully extend to a point where lip 394 of retainer 390 is disposed within and aligned with opening 314, as the diameter of opening 314 is slightly larger than the diameter of lip 394. However, as the diameter of lip 394 is larger than the distance across slot 312, retainer 390 is prevented from further horizontal movement along slot 312, even when force is applied. Thus, the inner probe shaft is locked in position with respect to the outer probe shaft, as well as retainer 390 being locked with respect to its ability to move horizontally along slot 312. However, the pressing of button 380 again allows a portion of middle area 398 to be aligned with slot 312, thus allowing retainer 390 to enter slot 312, in the direction of the force that is being applied.

If the button is no longer pressed while retainer is disposed within slot 312, slot 312 being smaller than the diameter of lip 394, will prevent retainer 390 and spring 400 from moving in a vertical direction and lip 394 will remain disposed under slot 312. In this position, the inner and outer probe shafts and retainer 390 are not locked in position and by applying force, retainer 390 will move horizontally along slot 312 in the direction of the force until it reaches one of the openings 314. Once retainer 390 reaches an opening 314, it becomes locked in position as described above, thus, also causing spring 400 to fully extend and button 380 to pop up to its upright position.

The slot 312 is shown having three openings 314, such number is not limiting and any number of openings 314 is within the scope of the invention and may be provided depending characteristics and features of the inner and outer probes of the composite probe. Like grooves 38a–38d of FIGS. 1 through 3, openings 314 may also correspond to certain holes or apertures, as well as other features, disposed at end 310 of inner probe shaft 306.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A surgical probe for use with a valve, comprising:
    an inner cannula having a first end and a second end and being operatively associated with said valve, said inner cannula also having an internal passageway extending therethrough from the first end to the second end; and
    an outer cannula having a first end and a second end and being operatively associated with said inner cannula, said outer cannula also having an internal passageway extending therethrough from the first end to the second end of said outer cannula, at least a portion of said inner cannula disposed within the internal passageway of said outer cannula;
    wherein either said inner cannula or said outer cannula is moved in relation with the other cannula to allow said probe to perform various suction and irrigation functions associated with laparascopic and endoscopic surgery.

2. A surgical probe for use with a valve, comprising:

an inner cannula having an inner probe shaft and an inner shaft housing, said inner probe shaft having a first end and a second end, said inner shaft housing having a first end and a second end, the first end of said inner probe shaft connected to the second end of said inner shaft housing, said first end of said inner shaft housing operatively associated with the valve; and an outer cannula having an outer probe shaft and an outer shaft housing, said outer probe shaft having a first end and a second end, said outer shaft housing having a first end and a second end, the first end of said outer probe shaft connected to the second end of said outer shaft housing, at least a portion of said inner cannula disposed within said outer cannula;

wherein either said inner cannula or said outer cannula is moved in relation with the other cannula to allow said probe to perform various suction and irrigation functions associated with laparascopic and endoscopic surgery.

3. The surgical probe of claim 2 wherein said inner probe shaft defining a first internal passageway extending from the first end to the second end of said inner probe shaft, said inner shaft housing defining a first internal channel extending from the first end to the second end of said inner shaft housing, said first internal passageway communicating with said first internal channel when said inner probe shaft is connected to said inner shaft housing, said outer probe shaft defining a second internal passageway extending from the first end to the second end of said outer probe shaft, said outer shaft housing defining a second internal channel extending from the first end to the second end of said outer shaft housing, said second internal passageway communicating with said second internal channel when said outer probe shaft is connected to said outer shaft housing.

4. The surgical probe of claim 3 wherein said second internal passageway is sized larger in diameter than said inner probe shaft's diameter and said second internal channel is sized larger in diameter than the second end of said inner shaft housing's diameter.

5. The surgical probe of claim 2 further including means for retaining at least a portion of said inner probe shaft within said outer probe shaft.

6. The surgical probe of claim 5 wherein said means for retaining comprises a detent disposed at the second end of said inner shaft housing and a correspondingly shaped groove disposed within an inner surface of said outer shaft housing.

7. The surgical probe of claim 2 wherein said inner probe shaft having an inner surface and an outer surface and said outer probe shaft having an inner surface and an outer surface, said surgical probe further including means for sealing a space created between said inner surface of said outer probe shaft and said outer surface of said inner probe shaft when said inner probe shaft is received within said outer probe shaft.

8. The surgical probe of claim 7 wherein said means for sealing is an o-ring disposed along the outer surface of said inner probe shaft or disposed within said outer shaft housing.

9. The surgical probe of claim 2 further including means for providing a tension fit between said inner probe shaft and said outer probe shaft when said inner probe shaft is received within said outer probe shaft.

10. The surgical probe of claim 9 wherein said means for providing is a retaining ring disposed along an outer surface portion of said inner probe shaft or disposed within said outer shaft housing.

11. The surgical probe of claim 2, further including means for determining the position of said inner probe shaft with respect to said outer probe shaft.

12. The surgical probe of claim 11 wherein said means for determining includes at least one groove disposed within an inner surface of said outer shaft housing and a detent disposed at the second end of said inner shaft housing.

13. The surgical probe of claim 12 wherein each said groove corresponds to a specific position of said inner probe shaft with respect to said outer probe shaft.

14. The surgical probe of claim 2, further including means for positioning said inner probe shaft with respect to said outer probe shaft.

15. The surgical probe of claim 14 wherein said means for positioning comprises an elongated slot disposed along a portion of said inner shaft housing and a spring-actuated locking means, a portion of said locking means disposed within said slot.

16. The surgical probe of claim 15 wherein said locking means comprises a button member, spring means and retainer member, a first end of said retainer member inserted through said spring means and attached to said button member, a second end of said retainer member being disposed within said slot, wherein by depressing said button member, said retainer member may be moved along said slot to position or move said inner probe shaft with respect to said outer probe shaft.

17. The surgical probe of claim 15, further including means for determining the position of said inner probe shaft with respect to said outer probe shaft.

18. The surgical probe of claim 17 wherein said means for determining includes at least one aperture disposed along said slot.

19. The surgical probe of claim 18 wherein each said aperture disposed along said slot corresponds to a specific position of said inner probe shaft with respect to said outer probe shaft.

20. A surgical probe for use with a valve, comprising:

an inner cannula having an inner probe shaft defining a first internal passageway extending from a first end to a second end of said inner probe shaft and an inner shaft housing defining a first internal channel extending from a first end to a second end of said inner shaft housing, the first end of said inner probe shaft connected to the second end of said inner shaft housing to allow communication between said first internal passageway and said first internal channel, the first end of said inner shaft housing operatively associated with the valve;

an elongated slot extending along a portion of said inner shaft housing;

an outer cannula having an outer probe shaft defining a second internal passageway extending from a first end to a second end of said outer probe shaft and an outer shaft housing defining a second internal channel extending from a first end to a second end of said outer shaft housing, the first end of said outer probe shaft connected to the second end of said outer shaft housing to allow communication between said second internal passageway and said second internal channel, at least a portion of said inner probe shaft disposed within said second internal channel and said second internal passageway, at least a portion of the second end of said inner shaft housing disposed within said second internal channel;

a spring-actuated locking means operatively associated with said outer shaft housing, a portion of said locking means disposed within said slot;

an o-ring disposed along an outer surface portion of said inner probe shaft, said o-ring providing a blockage seal for material and debris entering the space created between said inner probe shaft and said outer probe shaft when said inner probe shaft is inserted within the second internal passageway of said outer probe shaft; and a retaining ring disposed along an outer surface portion of said inner probe shaft intermediated said o-ring and the first end of said inner probe shaft, said retaining ring providing a tension fit between said inner probe shaft and said outer probe shaft when said inner probe shaft is received within said outer probe shaft;

wherein either said inner cannula or said outer cannula is moved in relation with the other cannula to perform various functions.

21. The surgical probe of claim 20 wherein said locking means comprises a button member, spring means and retainer member, a first end of said retainer member inserted through said spring means and attached to said button member, a second end of said retainer member being disposed within said slot, wherein by depressing said button member, said retainer member may be moved along said slot to position or move said inner probe shaft with respect to said outer probe shaft.

22. The surgical probe of claim 21, further including means for determining the position of said inner probe shaft with respect to said outer probe shaft.

23. The surgical probe of claim 22 wherein said means for determining includes at least one aperture disposed along said slot.

24. The surgical probe of claim 23 wherein each said aperture disposed along said slot corresponding to a specific position of said inner probe shaft with respect to said outer probe shaft.

* * * * *